(12) United States Patent
Beard

(10) Patent No.: US 7,672,793 B2
(45) Date of Patent: Mar. 2, 2010

(54) METHOD FOR CALCULATING PROBABILISTIC DAMAGE SIZES IN STRUCTURAL HEALTH MONITORING SYSTEMS

(75) Inventor: Shawn J. Beard, Livermore, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 204 days.

(21) Appl. No.: 12/040,550

(22) Filed: Feb. 29, 2008

(65) Prior Publication Data

US 2008/0255776 A1    Oct. 16, 2008

Related U.S. Application Data

(60) Provisional application No. 60/912,112, filed on Apr. 16, 2007.

(51) Int. Cl.
*G06F 17/18* (2006.01)
(52) U.S. Cl. .............................. 702/35; 702/181; 73/598
(58) Field of Classification Search .................. 702/35, 702/181
See application file for complete search history.

(56) References Cited

U.S. PATENT DOCUMENTS

| | | | |
|---|---|---|---|
| 6,597,997 B2* | 7/2003 | Tingley | 702/34 |
| 7,458,266 B2* | 12/2008 | Beard et al. | 73/579 |
| 2006/0095877 A1* | 5/2006 | Su et al. | 716/5 |
| 2008/0289423 A1* | 11/2008 | Gordon et al. | 73/602 |

\* cited by examiner

*Primary Examiner*—Bryan Bui
*Assistant Examiner*—Jonathan Teixeira Moffat
(74) *Attorney, Agent, or Firm*—Innovation Counsel LLP

(57) ABSTRACT

A method for calculating the probable damage size in a structure includes defining a configuration of an array of transducers mounted on the structure. Any pair of the transducers includes an actuator and a sensor, and each pair defines a propagation path in the structure. All propagation paths that are affected by being touched by a damage of the structure, and all adjacent paths that are untouched and thereby unaffected by the damage, are identified. A range of sizes of the damage is determined, and a probability density of the damage versus damage size is calculated on the basis of the transducer array configuration and the affected and unaffected propagation paths identified. On the basis of the probability density, a most probable damage size is determined, and the probability of the damage being greater or less than the most probable damage size is also determined.

6 Claims, 4 Drawing Sheets

METHOD FOR CALCULATING PROBABILISTIC DAMAGE SIZES IN STRUCTURAL HEALTH MONITORING SYSTEMS

CROSS-REFERENCE TO RELATED APPLICATIONS

This application claims the benefit of U.S. Provisional Patent Application No. 60/912,112, entitled "STRUCTURAL HEALTH MONITORING SYSTEM AND METHODS FOR USE," filed Apr. 16, 2007, the entire disclosure of which is incorporated herein by reference.

TECHNICAL FIELD

This invention relates generally to structural health monitoring (SHM) systems. More specifically, this invention relates to the calculation of probabilistic damage sizes and placing associated upper bounds on the damage sizes calculated in such systems.

BACKGROUND

The diagnostics and monitoring of structures for damage, such as that carried out in the structural health monitoring (SHM) field, are often accomplished by employing arrays of transducers. The transducers are often used as both actuators and sensors, and typically comprise piezoelectric transducers, e.g., lead-zirconate-titanate (PZT) transducers, which are bonded to the structure to excite elastic waves at ultrasonic frequencies that propagate along paths on the surface of the structure or through the structural medium. When damage occurs on or in the structure between the transducers, the associated actuator-sensor propagation paths are affected by the damage, resulting in changes to the signals received at the sensors indicative of the location, size and type of the damage. Knowing which actuator-sensor paths are affected is useful in determining the presence of damage and the approximate location of damage. However, there may not be direct information about the size of the damage. There is a need, therefore, for a method for determining the size of the damage, as well as methods for placing probabilistic bounds on the size of the damage detected.

SUMMARY

In numerous possible SHM system embodiments, damage in a structure is detected as a crack, opening or void that interferes with the propagation of an elastic wave signal through a structure between a actuator transducer and a sensor transducer mounted thereon, thereby causing attenuation of the direct line-of-sight propagating signal wave, i.e., the first arrival signal, or alternatively, causing scattering from the damage to be detected by other sensor transducers as secondary signals. The damage may be of a type that opens to the surface of the monitored structure, in which case the preferred mode of detection is via surface propagating elastic waves, or the damage may be embedded below the surface of the structure, in which case the preferred mode of detection is via bulk propagating elastic waves. The extent of the damage, e.g., the size thereof, may be determined by the propagation paths that are directly or indirectly affected thereby, i.e., those demonstrating attenuation of the first arrival signal, and by the extent of generation of secondary signals at adjacent transducers due to scattering.

In one embodiment, a method for calculating a probable damage size in a structural health monitoring system includes defining a configuration of an array of a plurality of transducers mounted on a structure, wherein any selected pair of transducers comprises an actuator and a sensor, and wherein each pair defines a signal wave propagation path in the structure. All propagation paths that are affected by being touched by a damage of the structure, as well as all propagation paths that are untouched and thereby unaffected by the damage, are identified. A range of sizes of the damage is determined. A probability density of the damage versus damage size is calculated on the basis of the transducer array configuration and the affected and unaffected propagation paths identified. On the basis of the probability density, a most probable damage size is found, and the probabilities of the damage either being greater or less than the most probable damage size are determined.

The above and other features and advantages of the present invention will be more readily apparent from a consideration of the detailed description of some exemplary embodiments thereof set forth below, particularly if taken in conjunction with the accompanying drawings, wherein the same or like elements are referred to by the same or like reference numerals throughout.

DETAILED DESCRIPTION

In a typical structural health monitoring (SHM) system, an array of transducers is attached to the structure. The transducers may be capable of both transmitting and sensing elastic waves that propagate through the structure. Pairs of such actuator-sensor transducers, where an actuator transmits and the sensor receives, establish selected elastic wave propagation paths within the structure. An elastic wave may be detected by direct propagation from the actuator to the sensor. If damage occurs on this direct path, the signal may be partially or entirely attenuated. Alternatively, if the damage is not located directly in the propagation path, but is offset therefrom, the damage may nevertheless be severe enough to reflect a wave originating from an actuator, and be detected by one or more receiving sensors as a secondary signal or pulse. In this latter case, the received secondary pulse will correspond to a longer propagation path, and a consequent longer transmission time, and so may thereby be distinguished from the direct signal.

If damage has been determined to be on one or more particular actuator-sensor direct paths (i.e., "affected paths"), then the geometry of the actuator-sensor paths (both affected paths and unaffected paths) can be used to determine the size of each damage in a statistical sense. That is, for each damage, a probability density curve for the damage size can be determined, giving an upper bound on the size, as well as the most probable size thereof.

The damage may be characterized as a circle and the calculations for the damage size are based on the geometry of the actuator-sensor paths. In order to be detected via a direct propagation path, the damage must touch the affected paths, i.e., the signal amplitude may then be affected (i.e., attenuated) by the existence of damage in the path. At the same time, by definition, the damage does not touch any of the unaffected paths, thus setting an upper bound on the damage size. The determination of whether there is damage in the affected path may be based on a signal threshold requirement.

Figure 1:
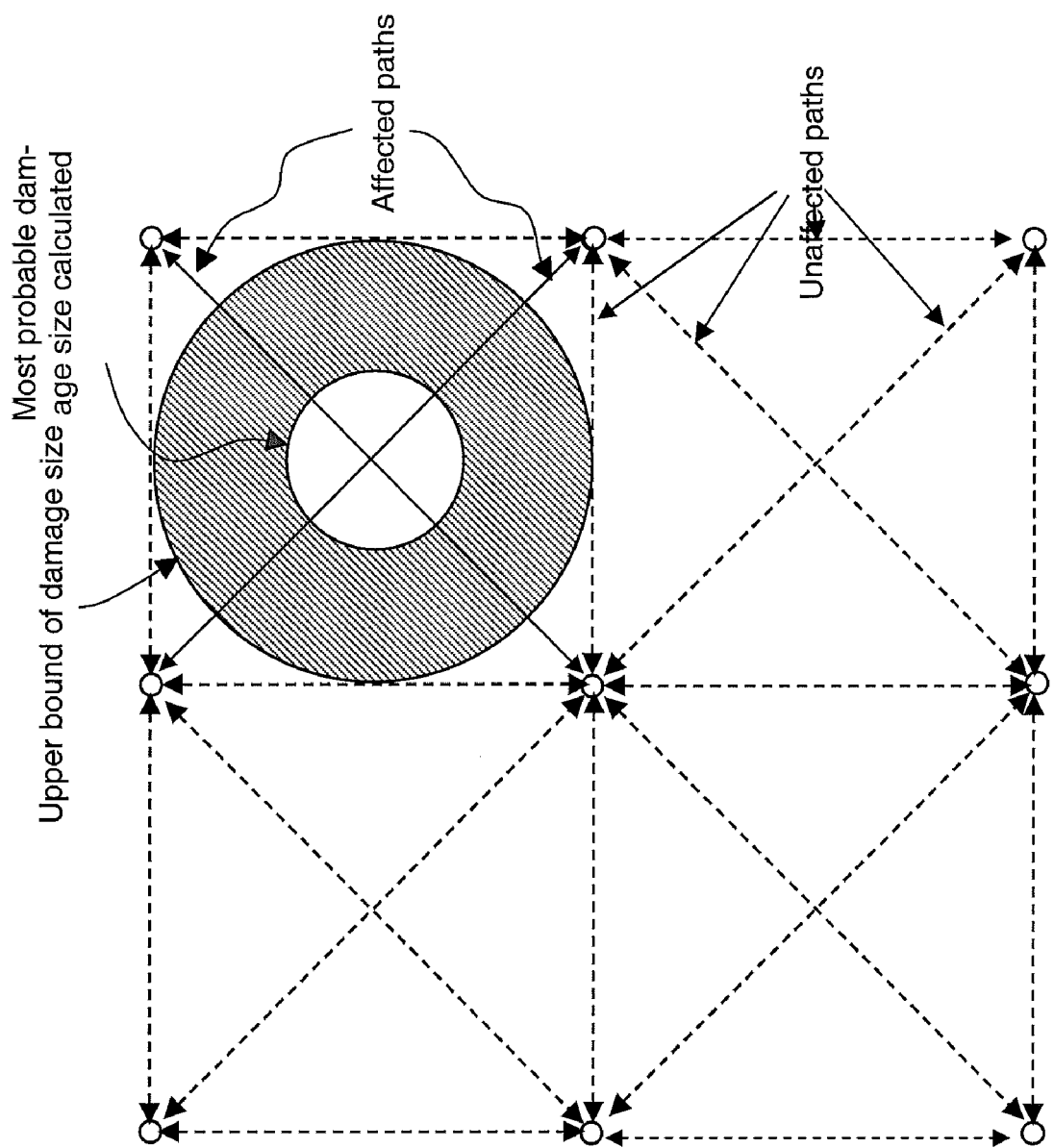
FIG. 1 illustrates an exemplary arrangement of actuator-sensor transducers and propagation paths for detecting damage, according to an embodiment of the disclosure.
Figure 2:
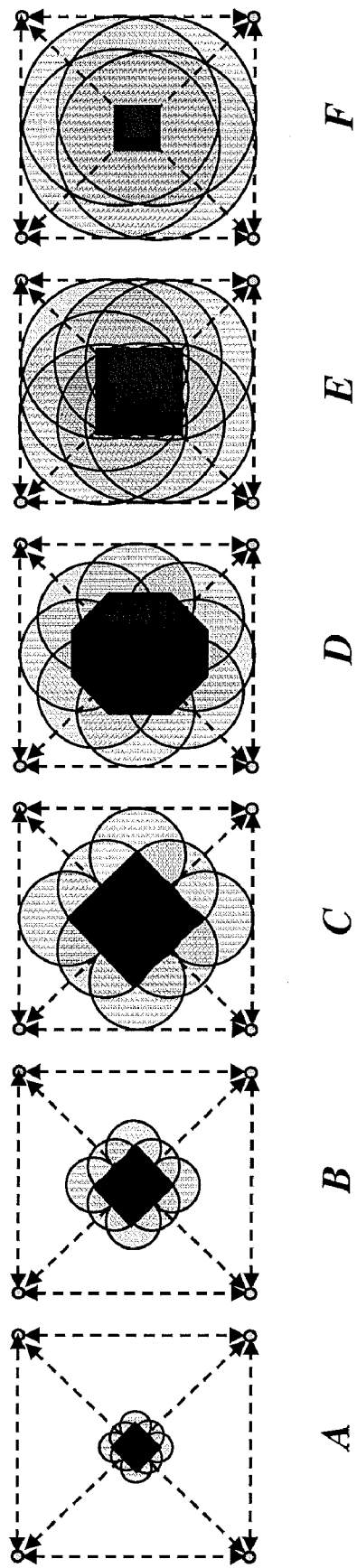
FIGS. 2A through 2F illustrate how damage centers may be located as a function of damage size according to an embodiment of the disclosure.

The nature of the geometry of the placement of actuators and sensors, i.e., the selected paths, determines the details of the calculation of the probabilistic damage size. FIG. 1 is an exemplary illustration of possible damage that intersects no more than two actuator-sensor paths in a square array of transducers. As above, a transducer may function as both an actuator and a sensor. That is, a transducer may both transmit and/or receive elastic waves in the structure. In the illustrated example, the transducers are arranged in a square array, and damage is presumed to intersect the two diagonal paths in a single square sub-array of transducers. That is, for the illustrated example, there are only two affected paths.

In the example of FIG. 1, the lower bound of the damage size, i.e., the smallest possible damage size, is a zero radius point located directly at the crossing point of the affected paths. Similarly, the largest damage that intersects both paths is a circle whose diameter is nearly, but not equal to or greater than, the side dimension of the square formed by the corner locations of the transducers. It may be noted that there is only one point at which the smallest size damage can be located. Similarly, the largest size damage must be located with its center at the same point. Damage of either extreme size is possible, but highly unlikely. This may be understood from the fact that the totality of locations in which the center of damage for either the smallest or the largest damage is a single point of zero dimension. Thus, the probability of a damage of either the largest or smallest size is substantially zero. Conversely, the probability of a damage occurring which is characterized as having a certain diameter intermediate of the two extrema increases in proportion to the area in which the damage center can be located and still intersect both of the affected paths.

Thus, for such intermediate damage sizes, the circle representing the diameter of the damage may be placed with its center in locations that cover an area which is limited by the requirement that the perimeter of the damage circle always crosses both sensor-actuator paths (in this case, the diagonals) but does not intersect the respective edge paths of the four transducers located at the corners of the sub-array. This area in which the damage center may be found, divided by the area of the sub-array, is proportional to the probability that the damage has the corresponding size. FIGS. 2A-2F illustrate how changing the size of the damage affects the possible locations in which the damage may be positioned and still intersect or touch only the identified affected paths, i.e., the diagonal paths. It can be seen that the central area grows from a point to a maximum value as the damage size increases, and then shrinks again to a point, as the damage grows to the maximum possible diameter. In the example illustrated, it may be seen that the highest probability of damage size is determined approximately by the dark area of FIG. 2D.

Figure 3:
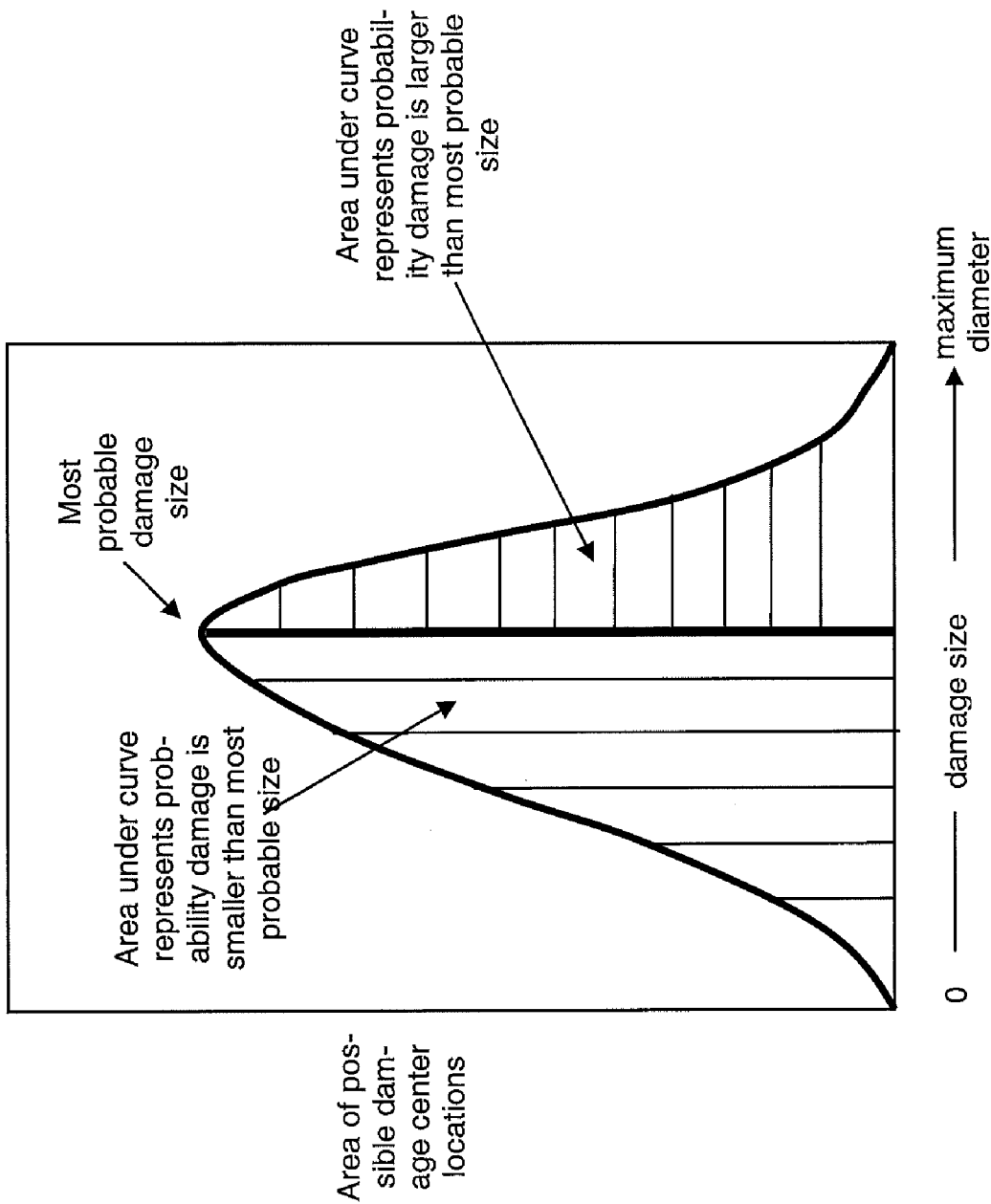
FIG. 3 is a probability density curve of the likelihood of a damage having various sizes according to the present disclosure.

FIG. 3 is a plot of the respective sizes of the central areas of FIGS. 2A-2F as a function of damage size, where the damage size is a continuous variable. The central area may be normalized to the size of the sub-array square dimension, and the vertical axis of FIG. 3 may thus be normalized so that the area under the curve has a total value of unity.

FIG. 3, when normalized in this way, becomes the probability density curve. The most probable damage size is then determined at the peak, or maximum of the curve. Physically, this peak represents the largest dark central area of FIGS. 2A-2F, as described above.

In addition to the most probable damage size, the percentage chance that the detected damage is smaller or larger than the most probable size can be computed as the respective areas under the curve above or below the most probable damage size. The percentage probability that the damage is smaller than the most probable size is the area under the curve to the left of this value, and the area under the curve above the most probable size is the percentage probability of its being larger than the most probable size.

The details of calculating the probability density, most probable damage size, and probability of damage being greater or less than the most probable size are affected by the details of the sensor-actuator geometry and the structure. A variety of numerical methods and curve fitting approximations are well known in the art, and are contemplated within the scope of the disclosure.

Figure 4:
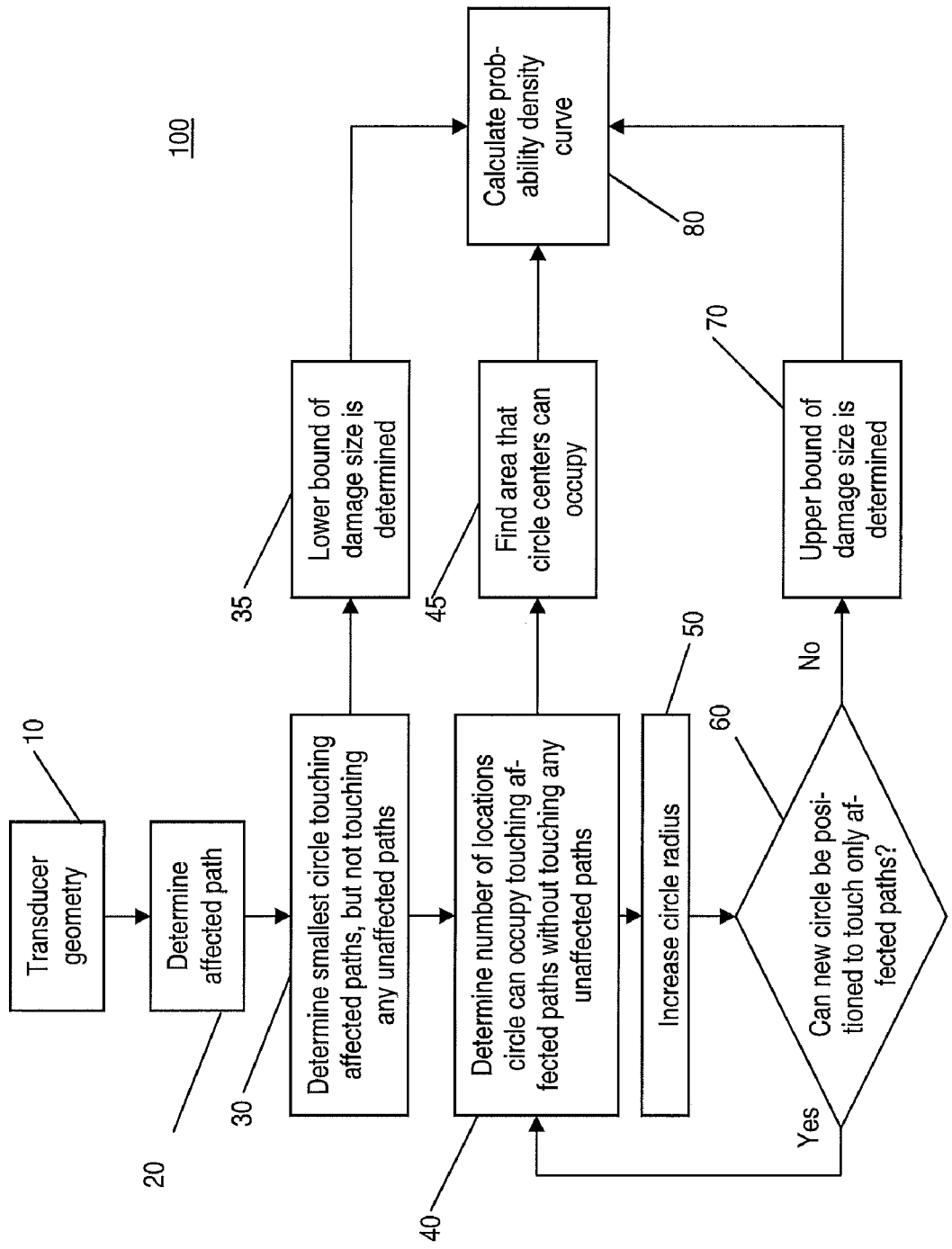
FIG. 4 is a flow diagram of a method 100 for determining the probabilistic size of damage according to the present disclosure.

FIG. 4 is a process flow diagram of a method 100 for determining the probabilistic size of damage for an actuator-sensor array in a SHM system. Method 100 includes specifying a configuration geometry (block 10) for locating transducers on the structure. After actuator-sensor propagation paths are defined, a damage location region enclosed by a selected group of transducers is identified in which the damage intersects a selected number of paths (the affected paths), and in which defined adjacent paths are not affected by the damage (block 20), i.e., paths adjacent to the damage, but which the damage does not touch, and therefore, does not affect.

Given the specified region in which the damage is located, a damage size may be posited that is characterized by a circle of an initial smallest radius (block 30) that touches all affected paths, but does not touch any defined unaffected paths. The smallest size damage then determines a lower bound of detected damage size (block 35). In the case of two intersecting paths, this is, by definition, a point, viz., the point of intersection of the paths. However, in some transducer arrays, it is possible that the two affected paths do not intersect, and thus, the smallest damage size may not be a point. The possible locations of the damage may be determined (block 40) to be a plurality of positions in which the damage touches all affected paths, but does not touch unaffected paths. The locations of the centers of all possible positions of the damage circle determines an area enclosing the centers (block 45) of the corresponding sized damage.

The radius of the posited damage circle may be incrementally increased by a selected amount (block 50). A determination is then made whether the new, larger damage circle so posited can be positioned so as to touch only the affected paths (decision block 60). If it is determined that the damage can be positioned in one or more locations (a "Yes" result in decision block 60), method 100 continues to step 40, in which the possible locations at which the center of the new damage circle may be positioned so as to touch the affected paths previously identified without also touching the unaffected paths previously identified. A new damage area is calculated (block 45) which encloses the centers corresponding to the new damage size.

When the damage circle radius is iteratively increased (block 50) in the foregoing manner, a "No" result will eventually occur at decision block 60, meaning that the newly incremented circle now no longer touches only the previously identified affected paths. Thus, an upper bound on the damage size is thereby determined (block 70), based on the last damage circle providing a Yes result in decision block 60. The upper and lower bound on damage size, and areas enclosing the damage centers corresponding to different damage sizes are combined to calculate the probability density curve (in block 80) described above in connection with FIG. 3, together with the most probable damage size (i.e., the peak or maximum of the curve), and the probabilities of the damage being either greater or less than the most probable size described above.

Although the present disclosure has been described with reference to certain exemplary embodiments thereof, it will be understood by those skilled in the art that a variety of modifications and variations may be made to these without departing from the spirit and scope of the present disclosure as defined in the appended claims, and their functional equivalents.

What is claimed is:

1. A method for calculating the probable damage size in a structure monitored by a structural health monitoring (SHM) system, the method comprising:
   defining a configuration of an array of transducers mounted on the structure, wherein corresponding pairs of transducers of the array comprise an actuator and a sensor, and wherein each corresponding pair of transducers defines a propagation path in the structure extending between the two transducers;
   identifying, using at least said array of transducers all propagation paths that are affected by being touched by a damage to the structure, wherein all propagation paths that are untouched are thereby unaffected by the damage;
   determining a range of sizes of the damage;
   calculating a probability density of the damage versus damage size on the basis of the transducer array configuration and the affected and unaffected propagation paths identified;
   finding a most probable damage size on the basis of the probability density; and,
   determining the probability of the damage being greater or less than the most probable damage size on the basis of the probability density.

2. The method of claim 1, wherein the determining of the range of damage sizes comprises:
   determining the smallest size of damage that can affect the affected propagation paths identified without affecting the unaffected propagation paths identified; and,
   determining the largest size of damage that can affect the affected propagation paths identified without affecting the unaffected propagation paths identified.

3. The method of claim 2, further comprising:
   varying the size of the damage in increments between the smallest and largest sizes of damage; and,
   determining for each damage size increment a corresponding area of the structure in which a center of the damage can be located and at which the damage touches the affected propagation paths identified without touching the unaffected propagation paths identified.

4. The method of claim 3, wherein the calculating of the probability density curve further comprises:
   computing the area under the curve of corresponding area versus damage size increment; and,
   normalizing the values of the corresponding areas by dividing all values by the total area under the curve.

5. The method of claim 4, wherein the finding of the most probable damage size comprises locating a maximum value of the probability density curve.

6. The method of claim 5, wherein the determining of the probability of the damage size being greater or less than the most probable damage size comprises calculating the respective areas under the probability density curve for damage sizes that are greater and less than the most probable damage size.

* * * * *